(12) United States Patent
Ho et al.

(10) Patent No.: US 8,232,092 B2
(45) Date of Patent: Jul. 31, 2012

(54) APPARATUS AND METHOD FOR DIGITAL MAGNETIC BEADS ANALYSIS

(75) Inventors: Winston Z. Ho, Hacienda Heights, CA (US); John Collins, Fullerton, CA (US)

(73) Assignee: Maxwell Sensors, Inc., Santa Fe Springs, CA (US)

( * ) Notice: Subject to any disclaimer, the term of this patent is extended or adjusted under 35 U.S.C. 154(b) by 516 days.

(21) Appl. No.: 12/069,720

(22) Filed: Feb. 11, 2008

(65) Prior Publication Data

US 2008/0234144 A1 Sep. 25, 2008

Related U.S. Application Data

(63) Continuation-in-part of application No. 11/502,606, filed on Aug. 9, 2006, now Pat. No. 7,871,770, and a continuation-in-part of application No. 11/580,514, filed on Oct. 13, 2006, now Pat. No. 7,858,307.

(60) Provisional application No. 60/706,896, filed on Aug. 9, 2005, provisional application No. 60/964,108, filed on Aug. 8, 2007.

(51) Int. Cl.
*C12M 1/34* (2006.01)
*G01N 21/00* (2006.01)
*C40B 60/12* (2006.01)

(52) U.S. Cl. ............... 435/283.1; 435/288.4; 435/288.7; 422/82.05; 422/82.07; 506/39

(58) Field of Classification Search .................. None
See application file for complete search history.

(56) References Cited

U.S. PATENT DOCUMENTS 4,546,067 A 10/1985 Irving et al.
(Continued)

FOREIGN PATENT DOCUMENTS

WO 02/064829 8/2002
(Continued)

OTHER PUBLICATIONS

International Search Report of Counterpart PCT Application No. PCT/US2008/008529.

*Primary Examiner* — Betty Forman
(74) *Attorney, Agent, or Firm* — Marshall, Gerstein & Borun LLP

(57) ABSTRACT

A micro bead having a digitally coded structure that is partially transmissive and opaque to light. The pattern of transmitted light is determined by to decode the bead. The coded bead may be structured a series of alternating light transmissive and opaque sections, with relative positions, widths and spacing resembling a 1D or 2D bar code image. To decode the image, the alternating transmissive and opaque sections of the body are scanned in analogous fashion to bar code scanning. The coded bead may be coated or immobilized with a capture or probe to effect a desired bioassay. The coded bead may include a paramagnetic material. A bioanalysis system conducts high throughput bioanalysis using the coded bead, including a reaction detection zone and a decoding zone. Alternative method for barcode determination is based on barcode pattern image processes. Microbeads can also be settled down to the bottom of the well in a microplate, so the barcode can be decoded by image processed directly. Therefore, multiple-analyte tests can be performed in one single well. Microplate is a standard format; each plate can have 96, 384, or 1536 patient samples. The bead image is taken with a conventional microscope and optical detector from the bottom of an optically clear microplate, and barcode pattern can be decoded by image software. Therefore, the whole bead experiment can be performed in the microplate without taking the beads out.

12 Claims, 17 Drawing Sheets

U.S. PATENT DOCUMENTS

| | | | |
|---|---|---|---|
| 5,354,977 | A | 10/1994 | Roustaei |
| 6,145,742 | A | 11/2000 | Drexler |
| 6,350,620 | B2 | 2/2002 | Chang |
| 6,416,949 | B1 | 7/2002 | Dower et al. |
| 6,420,482 | B1 | 7/2002 | Dominguez et al. |
| 6,432,630 | B1 | 8/2002 | Blankenstein |
| 6,602,602 | B1 | 8/2003 | Crivello |
| 6,630,307 | B2 | 10/2003 | Bruchez |
| 6,734,420 | B2 | 5/2004 | Empedocles |
| 6,773,886 | B2 | 8/2004 | Kaufman |
| 6,833,487 | B2 | 12/2004 | Pesce et al. |
| 7,115,230 | B2 | 10/2006 | Sundararajan et al. |
| 7,441,703 | B2 * | 10/2008 | Moon et al. ............. 235/454 |
| 7,858,307 | B2 | 12/2010 | Ho |
| 7,871,770 | B2 | 1/2011 | Ho |
| 2001/0041369 | A1 | 11/2001 | Chang et al. |
| 2002/0164271 | A1 | 11/2002 | Ho |
| 2003/0059764 | A1 * | 3/2003 | Ravkin et al. ............. 435/4 |
| 2003/0129654 | A1 | 7/2003 | Ravkin et al. |
| 2003/0203390 | A1 | 10/2003 | Kaye et al. |
| 2004/0115680 | A1 | 6/2004 | Garey et al. |
| 2004/0132205 | A1 | 7/2004 | Moon et al. |
| 2004/0152129 | A1 | 8/2004 | Garey et al. |
| 2004/0234898 | A1 | 11/2004 | Batishko et al. |
| 2005/0003556 | A1 | 1/2005 | Nagasawa |
| 2005/0009081 | A1 | 1/2005 | McFarland et al. |
| 2005/0042764 | A1 | 2/2005 | Sailor et al. |
| 2005/0244955 | A1 | 11/2005 | Allbritton |
| 2007/0099218 | A1 | 5/2007 | Ho |
| 2007/0148599 | A1 | 6/2007 | True |
| 2008/0038559 | A1 | 2/2008 | True |
| 2009/0201504 | A1 | 8/2009 | Ho et al. |
| 2010/0210477 | A1 | 8/2010 | Ho |

FOREIGN PATENT DOCUMENTS

| | | |
|---|---|---|
| WO | WO 02/064829 A2 | 8/2002 |
| WO | 2004/025563 | 3/2004 |
| WO | 2007/081410 | 7/2007 |

* cited by examiner

| | |
|---|---|
| 1 | 1 0 1 1 0 1 0 1 0 0 |
| 2 | 1 1 0 0 0 0 1 1 1 1 |
| 3 | 1 1 0 0 1 1 1 1 1 1 |
| 4 | 1 1 0 0 1 1 1 1 1 1 |
| 5 | 1 1 0 0 1 1 0 0 1 1 |
| 6 | 1 1 0 0 0 1 0 0 1 1 |
| 7 | 1 1 0 0 1 1 0 0 1 1 |

Figure 14

APPARATUS AND METHOD FOR DIGITAL MAGNETIC BEADS ANALYSIS

This application is a continuation-in-part application of U.S. patent application Ser. No. 11/502,606, filed Aug. 9, 2006, now U.S. Pat. No. 7,871,770 and U.S. patent application Ser. No. 11/580,514, filed Oct. 13, 2006, now U.S. Pat. No. 7,858,307 which claims the benefit of the priority of Provisional Patent Application No. 60/706,896, which was filed Aug. 9, 2005 and Provisional Patent Application No. 60/964,108, which was filed Aug. 8, 2007. This provisional application is fully incorporated by reference, as if fully set forth herein. All other publications and U.S. patent applications disclosed herein below are also incorporated by reference, as if fully set forth herein.

BACKGROUND OF THE INVENTION

1. Field of the Invention

The invention relates generally to assay beads and methods for use thereof to carry out multiplexed bioassays with digital magnetic beads, and more particularly multiplexed bioassays using micro-volume samples, such as protein and nucleic acid analysis.

2. Description of Related Art

As current research in genomics and proteomics produces more multiplexed data, there is a need for technologies that can rapidly screen a large number of nucleic acids and proteins in a very small volume of samples. Microarray, DNA chips, and protein chips have drawn a great deal of commercial interest. The assays are typically performed on a planar biochip platform by arraying and immobilizing DNA on a solid support via mechanical printing in the x-y position onto the microscope slide, by piezoelectric ink-jetting or by direct synthesis of DNA on the chip. However, mechanical contact printing is not very attractive because it prints one spot per contact that results in relatively large printing variations from spot to spot or batch to batch, inconsistent spot morphology, misprinting, and slide surface variations, all of which are undesirable for DNA microarray analysis. Further, distributing a small volume of liquid samples over a relatively large chip surface often encounters the problems of insufficient sample amounts or non-uniform distribution over the chip surface. These problems can cause incomplete reactions or very long reaction time.

Micro bead technology potentially overcomes many of the problems of microarray technology and provides better quality control of each probe, flexibility with the assembly of various type and amount of probes in an analysis, and convenience of doing analysis without mechanical printing. Existing micro bead approaches include (1) the incorporation of spherical beads or particles with spectrally distinguishable fluorophore, fluorescent semiconductor quantum dots, and (2) metallic rods with either bar coded color (absorption) stripes or black and white strips. Both fluorescence and barcode strip beads are identified by optical detection in reflective or emissive configuration. The problems of reflection configuration are (1) it is difficult to setup the collection optics in proper position, especially when the beads are in micrometer scale, and (2) the light collection efficiency is poor and the barcode contrast is low, especially when micro beads are in the micro flow system. The flow scatters light, which interferes with optical reflection or emissive detection. Further, fluorescent beads, the spectral range and the possible number of spectrally distinguishable labels, however, often limit the potential number of code variations. Many laser light sources are often needed to excite different fluorescent labels.

In addition, the validity of the coding signatures is another serious concern, since the incorporated coding elements in some cases may be lost; photo bleached, or interfered spectrally with the analytical signals. In the case of multi-metal (Au, Pt, Ni, Ag, etc) color micro rods, the encoding scheme suffers from the difficulty of manufacturing and the number of colors, based on different metal materials, is limited. Many 1D or 2D bar codes are recognized by their specific image patterns. Optical imaging method is used for recognition of these bar code patterns. Although high speed camera is available for capturing bar code images, pattern recognition is a slow and time consuming process. It often needs special software to analyze the images section by section. Therefore, it is difficult to identify hundreds or thousands of beads in a short time to improve throughput. The following patent documents disclose some of the systems that exhibit some of the deficiencies noted above.

U.S. Pat. No. 6,773,886 issued on Aug. 10, 2004, entire contents of which are incorporated herein by reference, discloses a form of bar coding comprising 30-300 nm diameters by 400-4000 nm multilayer multi metal rods. These rods are constructed by electrodeposition into an alumina mold; thereafter the alumina is removed leaving these small multilayer objects behind. The system can have up to 12 zones encoded, in up to 7 different metals, where the metals have different reflectivity and thus appear lighter or darker in an optical microscope depending on the metal type whereas assay readout is by fluorescence from the target, and the identity of the probe is from the light dark pattern of the barcodes.

U.S. Pat. No. 6,630,307 issued on Oct. 7, 2003, entire contents of which are incorporated herein by reference, discloses semiconductor nano-crystals acting as a barcode, wherein each semiconductor nanocrystal produces a distinct emissions spectrum. These characteristic emissions can be observed as colors, if in the visible region of the spectrum, or may be decoded to provide information about the particular wavelength at which the discrete transition is observed.

U.S. Pat. No. 6,734,420 issued on May 11, 2004, entire contents of which are incorporated herein by reference, discloses an identification system comprising a plurality of identifiable elements associated with labels, the labels including markers for generating wavelength/intensity spectra in response to excitation energy, and an analyzer for identifying the elements from the wavelength/intensity spectra of the associated labels.

U.S. Pat. No. 6,350,620 issued on Feb. 26, 2002, discloses a method of producing a micro carrier employing the shape, size, and color of the carrier as image bar codes for identification. The patent discloses an identification system comprising a bar code is formed on the substrate by photolithography, and then using nickel plates to hot compress the bar code onto the surface of bead to form a microcake-like particle. The bar code pattern can be classified by an imaging recognition system.

U.S. Pub. No. US2005/0003556 A1, entire contents of which are incorporated herein by reference, discloses an identification system using optical graphics, for example, bar codes or dot matrix bar codes and color signals based on color information signal for producing the affinity reaction probe beads. The color pattern is decoded in optical reflection mode.

U.S. Pub. No. US2005/0244955, entire contents of which are incorporated herein by reference, discloses a micro-pallet which includes a small flat surface designed for single adherent cells to plate, a cell plating region designed to protect the cells, and shaping designed to enable or improve flow-through operation. The micro-pallet is preferably patterned in a readily identifiable manner and sized to accommodate a single cell to which it is comparable in size.

What is needed is a digitally encoded micro bead that provides for high contrast and high signal-to-noise detection, and that provides for parallel and high-throughput bioanalysis, e.g., of proteins, pathogens, gene expression, single nucleotide polymorphism, nucleic acid-based tissue typing, cell or chromosome sorting, and transcriptional profiling that requires smaller volumes of fluid and rapid assay.

SUMMARY OF THE INVENTION

The present invention is directed to a bead or pallet that is digitally coded as represented by an image that provides for high contrast and high signal-to-noise optical detection to facilitate identification of the bead. The image is implemented by a physical structure having a pattern that is partially substantially transmissive (e.g., transparent, translucent, and/or pervious to light), and partially substantially opaque (e.g., reflective and/or absorptive to light) to light. The pattern of transmitted light is determined (e.g., by scanning or imaging), the code represented by the image on the coded bead can be decoded.

In one embodiment, the coded bead comprises a body having a series of alternating light transmissive and opaque sections, with relative positions, widths and spacing resembling a 1 D or 2D bar code image (e.g., a series of narrow slits (e.g., 5 microns in width) representing a "0" code and wide slits (e.g., 10 microns in width) representing a "1" code, or vice versa). To decode the image, the alternating transmissive and opaque sections of the body are scanned with light (in analogous fashion to a bar code scanning process) or imaged (e.g., with a CCD sensor) to determine the code represented by the image determined from the transmitted light.

In one embodiment, the coded bead comprises a body having a series of alternating light transmissive and opaque sections, with relative widths bar code image (e.g., a series of narrow slits representing a "0" code and wide slits representing a "1" code, or vice versa). When the bead is illuminated with a light beam, based on either the "total intensity" of the transmission peak or the "bandwidth" of the transmission peak from the slit, the digital barcode either 0 or 1 can be determined by a line scan camera, a frame grabber, and a digital signal processor.

In one embodiment, the bar code pattern with a series of narrow and wide bands provides an unambiguous signal and differentiation for 0's and 1's. The position of the slits on the pallet will determine which of the bits is the least significant (LSB) and most significant bit (MSB). The LSB will be placed closer to the edge of the pallet to distinguish it from the MSB at the other, longer end.

In one embodiment, the coded bead is provided with a reflective thin film, (e.g., plating or coating the coded bead with a metal thin film, or providing an intermediate layer of metal thin film) to improve contrast and optical efficiency for image recognition for decoding.

One alternate embodiment may include a metal layer as a layer sandwiched between two polymeric layers, by appropriately modifying the above described process. With this embodiment, surface condition could be made the same for both exposed planar surfaces of the bead, to provide similar surface coating and immobilization conditions. Another embodiment is to coat the bead with polymer or functional molecules, such as biotin, carboxylated, or streptavidin; therefore, the whole bead has the same condition for molecular immobilization.

In one embodiment, the body of the coded bead may be configured to have at least two orthogonal cross sections that are different in relative geometry and/or size. Further, the geometry of the cross sections may be symmetrical or non-symmetrical, and/or regular or irregular shape. In one embodiment, the longest orthogonal axis of the coded bead is less than 1 mm.

In another aspect of the present invention, a microfluidic apparatus comprises a micro flow channel sized and configured to guide coded beads to advance one at a time pass a decoding. The decoding zone includes a code detector (a light scanner, a CCD sensor, etc.) that detects the pattern of transmitted light through each coded bead for decoding the code represented by the image thereon. The flow channel of the microfluidic apparatus has an internal cross section that has a geometry that is sized and shaped to receive and allow the coded bead to pass through when a particular cross section of the coded bead is aligned with the cross section of the micro flow channel, thereby presenting the coded bead in a particular orientation with respect to the decoding zone. In one embodiment, the geometry of the internal cross section of the flow channel is sized and shaped to receive and allow the coded bead to pass through when the smallest cross section of the coded bead is aligned with the micro flow channel (e.g., the long axis of the coded bead is aligned with the axis of the flow channel). The microfluidic apparatus may include more than one micro flow channel, to provide decoding of coded beads in parallel channels.

In another aspect of the present invention, a microfluidic apparatus comprises a micro flow channel sized and configured to guide coded beads to advance one at a time pass a decoding. The decoding zone includes a code detector (a light scanner, a CCD sensor, etc.) that detects the pattern of transmitted light through each coded bead for decoding the code represented by the image thereon. The flow channel of the microfluidic apparatus has an internal cross section that has a geometry that is sized and shaped to receive and allow the coded bead to pass through when a particular cross section of the coded bead is aligned with the cross section of the micro flow channel, thereby presenting the coded bead in a particular orientation with respect to the decoding zone. In one embodiment, the geometry of the internal cross section of the flow channel is sized and shaped to receive and allow the coded bead to pass through when the smallest cross section of the coded bead is aligned with the micro flow channel (e.g., the long axis of the coded bead is aligned with the axis of the flow channel). The microfluidic apparatus may include more than one micro flow channel, to provide decoding of coded beads in parallel channels.

In another aspect of the present invention, a microfluidic apparatus comprises a sheath flow system to provide steady and stable bead flow through the optical detection area. The sheath system includes one core flow, which carries the barcode beads, and two sheath flows, on the sides of or about or around the outer periphery of the core flow, pull the core flow into a proper dimension. The sheath flows, at much higher speed, can be pushed or pulled by vacuum, gravity, or pressure. By this method, the coded bead will align themselves in line and flow reliably, without wobbling or flipping, in the core flow channel through the detection zone. By adjusting the relative flow rate of core flow and sheath flows, the coded beads flow reliably in the flow system, thus it can be decoded and detected by an optical system accurately.

In another aspect of the present invention, the optical detection system consists of at least one illumination light source for barcode illumination and fluorescence detection. The wavelength of fluorescence excitation light source depends on the selection of the fluorophore. For example, a line scan CCD camera for barcode detection provides continuously scan at a rate of 65,000 scans/second. By proper adjusting the flow rate, each bead will be scanner several times under the illumination zone. Photon detector, such as photomultiplier tube, has the fast detection rate, such as 100 MHz. It is possible to quickly detect the barcode and fluorescence beads in the high speed flow system.

The identity of the bead may be associated with other properties and/or characteristics. In another aspect of the present invention, the coded bead is coated or immobilized with a biological and/or chemical substance, as a specific capture or probe to affect a desired bioassay or identification application. A plurality of beads may be applied to conduct multiplexed bioassays. For example the bead may be functionalized with a material selected from the group consisting of proteins, nucleic acids, small molecules, organic chemicals, inorganic chemicals, and combinations thereof, allowing for the possibility of multiplexed assays in homogeneous or heterogeneous media, using micro-volume samples.

In a further aspect of the present invention, a bioanalysis system is configured and structured for conducting bioanalysis using the coded bead of the present invention. The microfluidic system comprises the microfluidic apparatus to facilitate high throughput homogeneous or heterogeneous analysis. A detection zone of the microfluidic apparatus includes a reaction detector (e.g., a fluorescence detector, an absorption detector, a chemiluminescent detector, etc.) for detecting the result of reactions taken place on the coded beads. In one embodiment, the assay of the microfluidic system is configured and adapted for high-throughput analysis for immunoassay, gene expression, Single Nucleotide Polymorphism (SNP) diagnostics, DNA-based tissue typing, or transcriptional profiling.

In a further aspect of the present invention, a number of digital magnetic beads can be distributed on a planar surface and detected simultaneously with an image camera. The planar surface can be on a microslide or at the bottom of a microplate. The barcode patterns, representing digital signal such as "0" and "1", of each bead are determined by image processing. Microplate is a standard high throughput format in clinical diagnostics; each plate have 96, 384, or 1,536 patient samples.

In a further aspect of the present invention, the digital barcode beads have paramagnetic property, that is, they have magnetic property when placed within a magnetic field, but retain no residual magnetism when removed from the magnetic field. Magnetic beads allow washing in a microplate by collection of beads with an external magnet, and resuspension of beads when the magnetic field is removed. Multiple digital magnetic beads allow multiplexed assays to be performed in a single well.

In a further aspect of the present invention, a digital magnetic microbead analytical system comprises a. a microplate with a plurality of wells; b. at least one digital magnetic bead settled at the bottom of the wells of the microplate, c. an optical detector, located above or under the microplate, imaging the at least one magnetic microbead; and d. an image software to process the image pattern of at least one magnetic microbead. In one embodiment, the number of wells is between about 96, 384, or 1536 wells.

In a further aspect of the present invention, both bar-code image and fluorescence image are taken under a microscope and camera simultaneously. Therefore, the whole bead experiment can be performed in the microplate without taking the beads out.

In a further aspect of the present invention, the microbead analytical system, wherein the optical detector can detect the optical signal generated from the sensing chemistry and barcode image on the microbead.

In a further aspect of the present invention, the digital magnetic microbeads comprise a first layer; a second layer; and an intermediate layer between the first layer and the second layer, the intermediate layer having an encoded pattern defined thereon, wherein the intermediate layer is partially substantially transmissive and partially substantially opaque to light, representing a code corresponding to each of the microbeads.

In a further aspect of the present invention, the intermediate layer comprises a series of alternating substantially light transmissive sections and substantially light opaque sections defining the encoded pattern. The relative positions, widths and/or spacing between the transmissive sections and/or opaque sections represent a binary code. The substantially light opaque sections comprise a light blocking material. The body of each microbead has a longest orthogonal axis of 1 mm or less.

In a further aspect of the present invention, the first layer and the second layer of the digital magnetic beads are functionalized with a material selected from the group consisting of proteins, nucleic acids, small molecules, chemicals, and combinations thereof.

In a further aspect of the present invention, the light transmissive sections are defined by slits through the intermediate layer, and the light opaque sections are defined by a light reflective material and/or a light absorptive material. The slits comprise slits of a first width and slits of a second width, and wherein the first width represents a "0" and the second width represents a "1" in a binary code. The first width is about 1 to 10 microns and the second width is about 1 to 50 microns, and wherein the first width is narrower than the second width. The binary codes can be decoded by image software.

BRIEF DESCRIPTION OF THE DRAWINGS

For a fuller understanding of the scope and nature of the invention, as well as the preferred mode of use, reference should be made to the following detailed description read in conjunction with the accompanying drawings. In the following drawings, like reference numerals designate like or similar parts throughout the drawings.

FIG. 14 illustrates the digital code being determined based on the widths of the barcode present in each microbead.

DETAILED DESCRIPTION OF EMBODIMENTS OF THE INVENTION

The present description is of the best presently contemplated mode of carrying out the invention. This description is made for the purpose of illustrating the general principles of the invention and should not be taken in a limiting sense. The scope of the invention is best determined by reference to the appended claims.

For purposes of illustrating the principles of the present invention and not by limitation, the present invention is described herein below by reference to a micro bead that is in the shape of a pallet, and by reference to bioanalysis. However, it is understood that the present invention is equally applicable to micro beads of other overall geometries, and which are applied for other applications requiring identification based on the identity of the beads, without departing from the scope and spirit of the present invention. To facilitate discussion below, the micro bead of the present invention is referred to as a LITAB, which stands for a light transmitted assay bead.

Coded Bead

In one aspect of the present invention, a micro bead is digitally coded as represented by an image that provides for high contrast and high signal-to-noise optical detection to facilitate identification of the bead. The image is implemented by a physical structure having a pattern that is partially substantially transmissive (e.g., transparent, translucent, and/or pervious to light), and partially substantially opaque (e.g., reflective and/or absorptive to light) to light. The pattern of transmitted light is determined (e.g., by scanning or imaging), and the code represented by the image on the coded bead can be decoded. Various barcode patterns, such as circular, square, or shape, can be designed as long as it represented a "1" or "0" and can be recognized by the decoder.

Figure 2A:
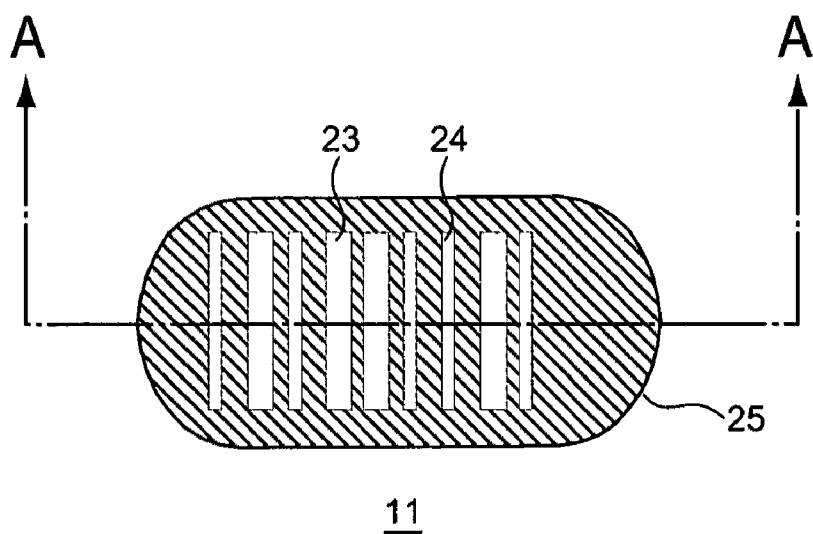
FIG. 2(a) is a top view of a LITAB in accordance with one embodiment of the present invention.
Figure 2B:
FIG. 2(b) is a sectional view taken along line A-A in FIG. 2(a)

In one embodiment, the coded bead comprises a body having a series of alternating light transmissive and opaque sections, with relative positions, widths and/or spacing resembling a 1 D or 2D bar code image (e.g., a series of narrow slits (e.g., about 1 to 5 microns in width) representing a "0" code and wide slits (e.g., about 1 to 10 microns in width) representing a "1" code, or vice versa, to form a binary code). FIG. 2 illustrates a coded bead, LITAB 11 in accordance with one embodiment of the present invention. The LITAB 11 has a body 25 in the shape of a flat pallet or disc. The body of the coded bead may be configured to have at least two orthogonal cross sections that are different in relative geometry and/or size. Further, the geometry of the cross sections may be symmetrical or non-symmetrical, and/or regular or irregular shape. In this particular embodiment, all three orthogonal axes are of different lengths, and the geometries of all three orthogonal cross sections are symmetrical and of regular shape. FIG. 2(a) shows that the planar geometry resembles a symmetrical stretched oval. FIG. 2(b) shows the cross section showing the longitudinal (or longest) axis. A series of wide and narrow slits 23 and 24 are provided through the body 25, which may be made of or coated with a substantially light opaque material (e.g., reflective or absorptive). The wide and narrow slits 23 and 24 represent a logical "1" and "0", respectively, or vice versa, and collectively represent a binary code (each slit representing a bit). In this embodiment, the code is analogous to a bar code. The narrow slits may have a width of 5 microns, and the wide slits 24 may have a width of 10 microns. For a LITAB having an overall dimension of 100× 50×10 μm to 200 μm×100 μm×20 μm, at least about 10 slits may be provided on the disc to encode 10 bits to 12 bits or more, allowing 1,024 to 4,096 or more unique codes. In one embodiment, the longest orthogonal axis of the coded bead is less than 1 mm.

Figure 2C:
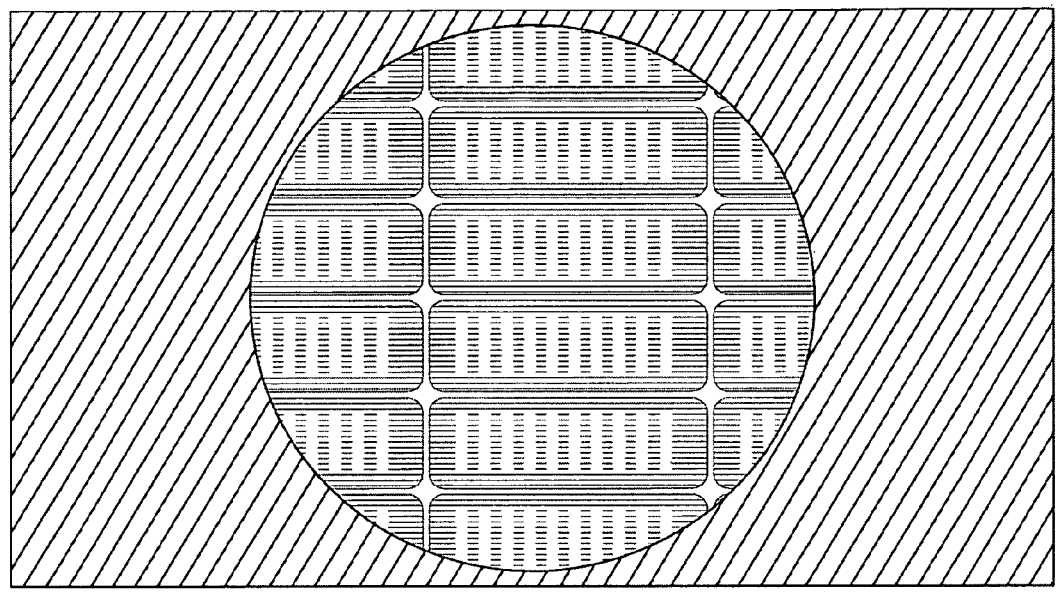
FIG. 2(c) is a top view of 10-digit barcode beads on a wafer.
Figure 2C:
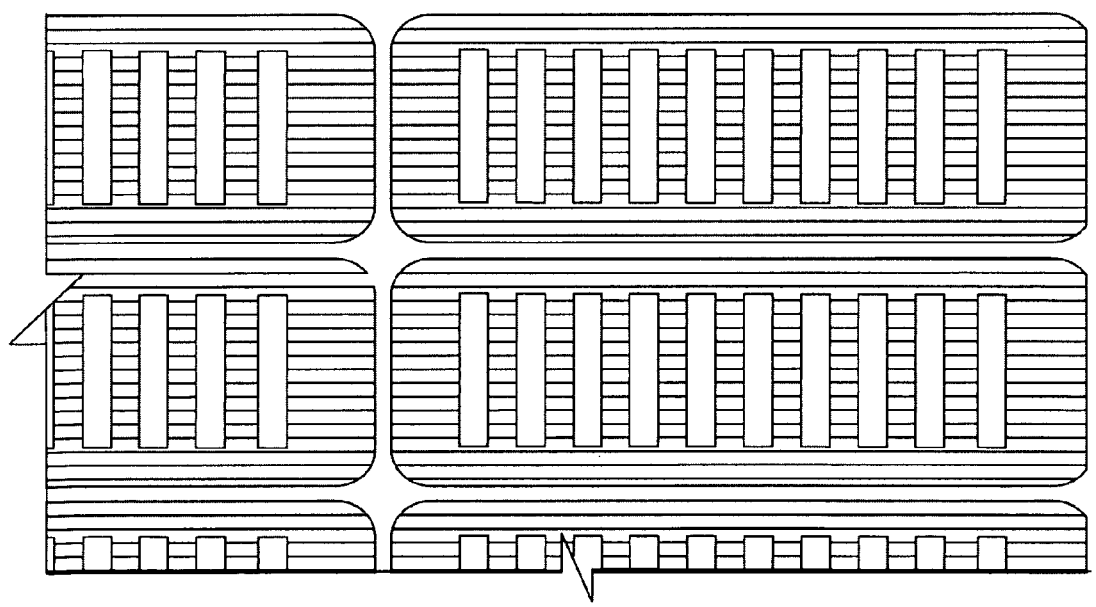
Figure 2D:
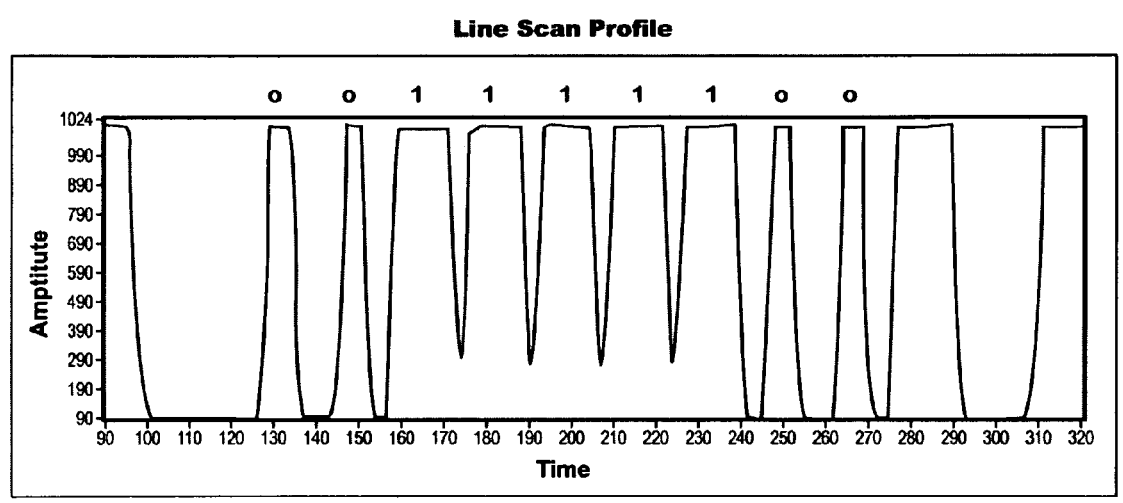
FIG. 2(d) shows the transmitted digital signal of a barcoded bead representing 0010110101.

While the illustrated embodiment shows a pattern of slits of spaced apart narrow and wide width, it is also possible to use a pattern of slits having a constant width which are spaced apart at narrow and wide spacings between adjacent slits to represent 1's and 0's, without departing from the scope and spirit of the present invention. FIG. 2(c) shows 10-digit LITABs on a wafer. The slit dimensions are 10 μm and 20 μm representing "1" and "0", respectively. FIG. 2(d) shows the transmission peaks of a single bead on the computer screen. When the bead is illuminated with a light beam, based on the either the "total intensity" of the transmission peak or the "bandwidth" of the transmission peak from the slit, the digital barcode either 0 or 1 can be determined by a line scan camera and a digital signal processor. Based on the figure, the barcode patterns can be easily identified based on the peak widths. The beads show 10-digit barcodes representing 0010110101.

Figure 3:
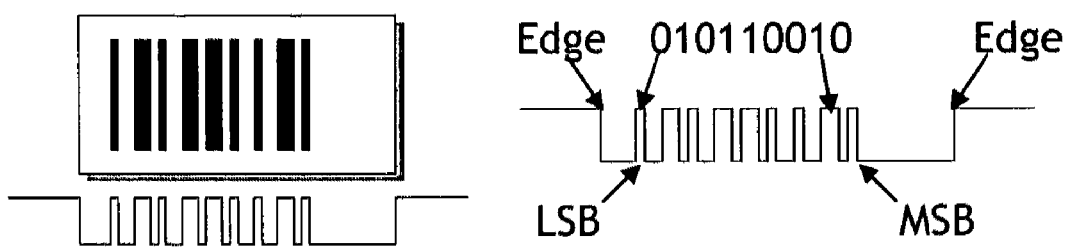
FIG. 3 illustrates the optical signal pulses representing light transmitted through the pattern of slits in a LITAB.

To decode the image, the alternating transmissive and opaque sections of the body are scanned with light (in analogous fashion to a bar code scanning process) or imaged (e.g., with a CCD sensor) to determine the code represented by the image determined from the transmitted light. For illustration purposes, FIG. 3 shows a series of signal pulses representing the detection of light transmitted through the slits 23 and 24 in the LITAB 11 in FIG. 2(a). The signal pulses correspond to the contrast of transmitted versus blocked light across the longitudinal axis of the LITAB 11. The width of each signal pulses represents a "1" or a "0" in the code of the LITAB 11. In the particular illustrated example, the wider pulses represent 1's and the narrow pulses represent 0's. The relative positions of the slits on the LITAB 11 determine which of the bits is the least significant bit (LSB) or the most significant bit (MSB). In one embodiment, the least significant bit was placed closer to one edge or end of the LITAB 11 to distinguish it from the most significant bit at the opposing edge or end. The concept of decoding the signal pulses is analogous to decoding for a traditional bar code.

In another embodiment, the size of the LITAB is sized and configured to be 150×50×10 μm, or proportionally smaller, and a slit width of about 2.5 μm. Each code on such a LITAB can consist of up to 14 slits (or bits), allowing 16,384 unique codes.

It is noted that in an alternate embodiment, the substantial transmissive section need not be a slit through the entire thickness of the body of the LITAB. The slit may be completely or partially filled with a substantially transparent or translucent material, which nonetheless provides substantially light transmissivity, compared to the opaque section.

For example, the LITAB may have a transparent body, covered with a light blocking material (e.g., a reflective material, or a light reflective or absorptive dye) that has openings defining slits exposing the transparent body. Light imaged on this LITAB would transmit light through the body at sections not covered by the blocking material (i.e., the slits), and block light in the covered section.

It is further noted that in the context of the concept of the present invention, the substantially opaque section need not completely block light transmission. It can be a section that substantially blocks light by substantially absorbing light or substantially reflecting light. The design concept is to achieve a high contrast in optical imaging, by relying on the high contrast of light transmissivity between the substantially transmissive section and the substantially opaque section. Compared to reflective or emissive bar code imaging practiced in the prior art, the present invention can achieve significantly higher contrast in the optical image, by detecting transmitted light in reference to blocked light. Also, in the context of the present invention, light transmissivity and opaqueness are reference to the particular frequency of the light from the anticipated light source to be used. For example, the opaque section may substantially block UV light, but may substantially transmit light outside the UV band. Similarly, the transmissive section may substantially transmit UV light, but may substantially block light outside the UV band.

In another embodiment, the coded LITAB can be provided with a reflective thin film or coating, (e.g., plating or coating the surface of the LITAB with a metal thin film, or providing an intermediate, sandwiched layer of metal thin film, or coating with a light absorptive dye) to improve contrast between transmitted versus blocked/reflected light and optical efficiency for image recognition for decoding, as discussed further discussed below.

The LITAB 11 may be fabricated using conventional methods used in thin film formation in a clean room microfabrication facility. The structure of the LITAB 11 may be obtained using processes that may include conventional photo-lithography, printing, silk-screening, curing, developing, etching (e.g., chemical etching, ion etching, and/or other removing processes), plating, dicing, and other process steps well known in the art for such types of structure and the material involved. The details of the steps in these processes have been omitted, as they may involve conventional patterning and photolithographic steps well known in semiconductor and/or micro-structure processing. The specific fabrication steps and materials involved, other than those specific steps and materials mentioned herein, when viewed alone are not a part of the present invention. It is noted that even though the disclosure herein may, by way of examples and not limitations, refer to specific coating, formation, patterning, deposition or other processes in connection with certain layers or structures, other processes may be substituted without departing from the scope and spirit of the present invention. There may be intermediate or interposing layers, coatings, or other structures present, and associated process steps present, which are not shown or discussed herein, but could be included without departing from the scope and spirit of the invention disclosed herein. For example, there may be buffer layers, primer layers, seed layers, adhesives, coatings, surface finishes, or other structures present. Other variations may be implemented without departing from the scope and spirit of the present invention.

Referring to FIG. 6(a) to (d), in one embodiment of the process for fabricating the LITAB, a layer 52 of Ti (e.g., 100 nm) is deposited by e-beam evaporation on a substrate 50, e.g., a clean glass slide (e.g., about 1 mm thick). Ti functions as a conducting seed layer as well as a surrogate releasing layer. The body 25 of the LITAB 11 may be formed using a layer of polymeric material. For example, a photoresist photopolymer (e.g., SU-8 and the like, as known in the art), may be utilized in creating the LITABs 11. A layer 21 of polymeric material is spin-coated on the Ti layer 52, and the slits 23 and 24 are formed in such layer using standard photolithographic procedures. For example, the slits 23 and 24 may be defined by UV-light irradiation using a photomask (not shown) defining the desired pattern of wide and narrow slits, and the planar shape of the LITAB body 25. An array of LITABs 11 may be formed on a single substrate, each having a different slit pattern representing a different code. The photomask may also define the periphery of the array of LITAB bodies, such that the LITAB bodies are separated from one another at the end of the same photolithographic process that defines the slits. Because SU-8 is transparent, an e-beam evaporator is utilized to deposit a metal layer, such as gold (Au, 0.1 μm) top layer 22 (see also FIG. 1(b)) on the SU-8 layer 21 supported on the substrate 50. The individual LITAB bodies 25 (shown in FIG. 2(b)) are finally freed from the underlying substrate 50 by dissolving the surrogate Ti layer 52 with an etching solution containing hydrofluoric acid (HF). In this way, the gold pattern on the LITAB blocks light by reflecting light (directed to both from the side exposed and the side adjacent to the SU-8 layer 21), and slits not covered by gold layer transmit light. Because the gold layer 22 blocks the light, while the open slits transmit the light, LITAB "bar codes" provide high optical signal, and high optical contrast when the transmitted light is detected.

An alternate embodiment may include a metal or a reflective non-metal layer as a layer sandwiched between two polymeric layers, by appropriately modifying the above described process. With this embodiment, surface condition could be made the same for both exposed planar surfaces of the LITAB, to provide similar surface coating and immobilization conditions, as will be discussed below. As in the previous embodiment, the thin metal layer enhances the signal contrast ratio of the transmitted light detection.

Figure 7:
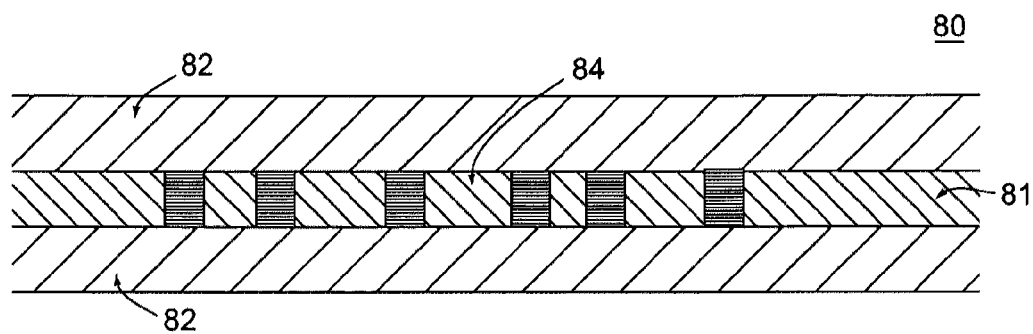
FIG. 7, illustrates a metal layer as a layer sandwiched between two polymeric layers that may provide the same surface chemistry for molecule immobilization.

FIG. 7 shows an alternate embodiment of a LITAB 80, which may include a metal layer 81 as an intermediate layer sandwiched between two SU-8 layers 82. The two SU-8 layers are designated as the first layer and second layer in the claim. A barcode pattern is fabricated on the metal layer 81. For example, slits 84 of different widths and/or spacings are formed in the metal layer 81. In the illustrated embodiment, the SU-8 layers 82 are closed layers (i.e., no slits). The process for forming the LITAB 80 may include first forming a first SU-8 layer 82, then forming the metal layer 81 followed by etching the slits 84 therein. A second SU-8 layer 82 is formed on the metal layer 81 (e.g., by spin coating and curing), which fills the slits 84. Alternatively, the slits 84 may be first filled with another transparent material, before forming the second SU-8 layer 82. With this embodiment, surface condition could be made the same for both exposed planar surfaces of the LITAB, to provide similar surface coating and immobilization conditions. The other embodiment is to coat the LITAB with polymer or functional molecules, such as biotin, carboxylated, or streptavidin; therefore, the whole bead has the same condition for molecular immobilization.

Digital Magnetic Microbeads

To facilitate bioassays as will be apparent from further discussion below in connection with the microfluidic system, a paramagnetic material may be imbedded in the LITAB (e.g., as an intermediate layer in the LITAB), and sandwiched between the first layer and second layer of polymer films.

Because paramagnetic materials have a relatively small and positive susceptibility to the magnetic field, the LITAB can be immobilized at a desired location by an external magnetic field, and the LITAB can be mobilized when the external field is removed. Paramagnetic materials include magnesium, molybdenum, lithium, aluminum, nickel, and tantalum. However, for prior art there are magnetic beads and barcode beads, no magnetic material has been incorporated into the barcode microbeads. This is because the magnetic material being inherently dark brown, would not be compatible with the reflective bar code, which requires alternating dark and white lines. It is noted that the paramagnetic coating on the LITAB would also function as a light blocking material, so a reflective layer is not necessary. The present invention would allow decoding based on transmitted light, even in the presence of the paramagnetic material.

Synthesis of LITAB

The identity of the LITAB may be associated with other properties and/or characteristics for purpose of bioassays, for example. In another aspect of the present invention, the coded LITAB is coated or immobilized with a biological and/or chemical substance, as a specific capture or probe to effect a desired bioassay or identification application. A plurality of beads may be applied to conduct multiplexed bioassays. For example the bead may be functionalized with a material selected from the group consisting of proteins, nucleic acids, small molecules, organic chemicals, inorganic chemicals, and combinations thereof, allowing for the possibility of multiplexed assays in homogeneous or heterogeneous media, using micro-volume samples.

Figure 1A:
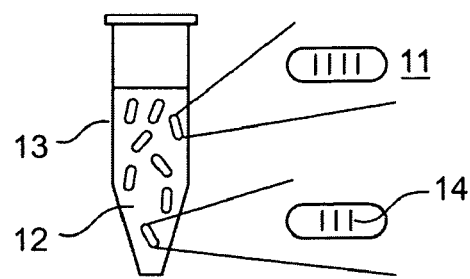
FIG. 1 illustrates the process for preparing Light Transmitted Assay Beads (LITAB) for bioassay, in accordance with one embodiment of the present invention: (a) Multiple LITAB in a tube, (b) LITAB for bioassay, and (c) a photo image of LITABs.
Figure 1B:
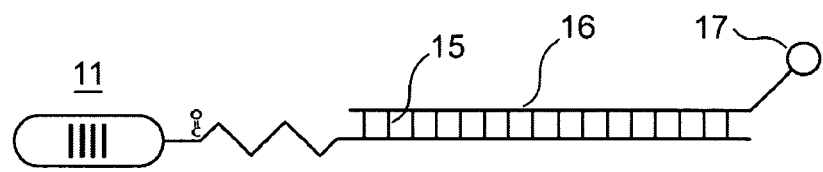
Figure 1C:
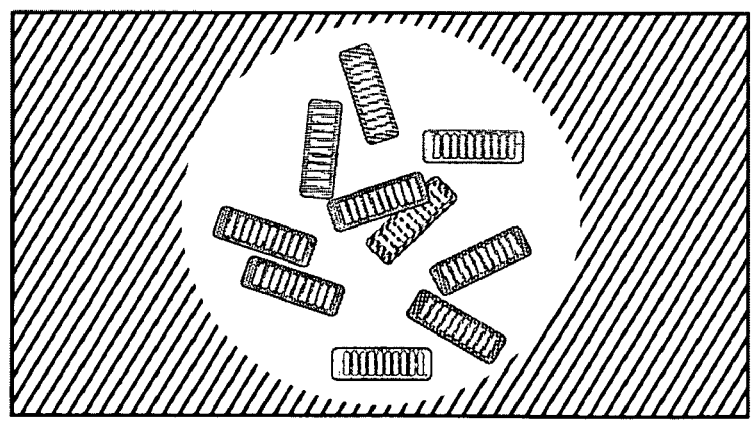

FIG. 1 illustrates an embodiment for preparing LITAB for bioassays. As shown in FIG. 1(a), the LITABs 11 allow multiplexed homogeneous bioassays on micro-volume samples. A mixture of LITABs 11 corresponding to different codes 14 are introduced into a small volume of biological sample 12 in a tube 13. The LITABs can be optically decoded easily and rapidly thereafter. In one embodiment, FIG. 1(b) shows one LITAB 11 functionalizing with nucleic acid probe 15 for target hybridization 16 and fluorescence detection 17. Several materials are available for bead immobilization. In one embodiment, the LITAB may be coated with a covalent DNA-binding agent used in microarray. The probe beads were subsequently hybridized in solution to a complementary oligo target which carried a covalently bound Cy5 fluorophore at its 5' end. FIG. 1(c) is an image of LITABs (size 200 µm×100 µm×20 µm) captured with a video microscope.

It is necessary for the LITAB material to have a similar or lower density than water or the intended solution used. Therefore, the LITABs 11 can homogeneously suspend in the aqueous solution for reactions. The LITAB material is configured to have about the same density as the liquid medium enabling the bead to suitably float in the medium. In addition, the material should be strong enough to be able to resist deformation that may result from sheer stresses during mixing and the like processes. As noted above, the body of the LITABs 11 may be made of a photoresist photopolymer such as the SU-8 photoresist polymer.

LITAB in Microfluidic System

In another aspect of the present invention, a microfluidic apparatus comprises a micro flow channel sized and configured to guide coded LITAB to advance one at a time pass a decoding zone. The decoding zone includes a code detector (a light scanner, a CCD sensor, etc.) that detects the pattern of transmitted light through each coded LITAB for decoding the code represented by the image thereon. The flow channel of the microfluidic apparatus has an internal cross section that has a geometry that is sized and shaped to receive and allow the coded LITAB to pass through when a particular cross section of the coded LITAB is aligned with the cross section of the micro flow channel, thereby presenting the coded LITAB in a particular orientation with respect to the decoding zone. In one embodiment, the geometry of the internal cross section of the flow channel is sized and shaped to receive and allow the coded LITAB to pass through when the smallest cross section of the coded LITAB is aligned with the micro flow channel (e.g., the long axis of the coded bead is aligned with the axis of the flow channel). The microfluidic apparatus may include more than one micro flow channel, to provide decoding of coded LITABs in parallel channels.

Figure 4A:
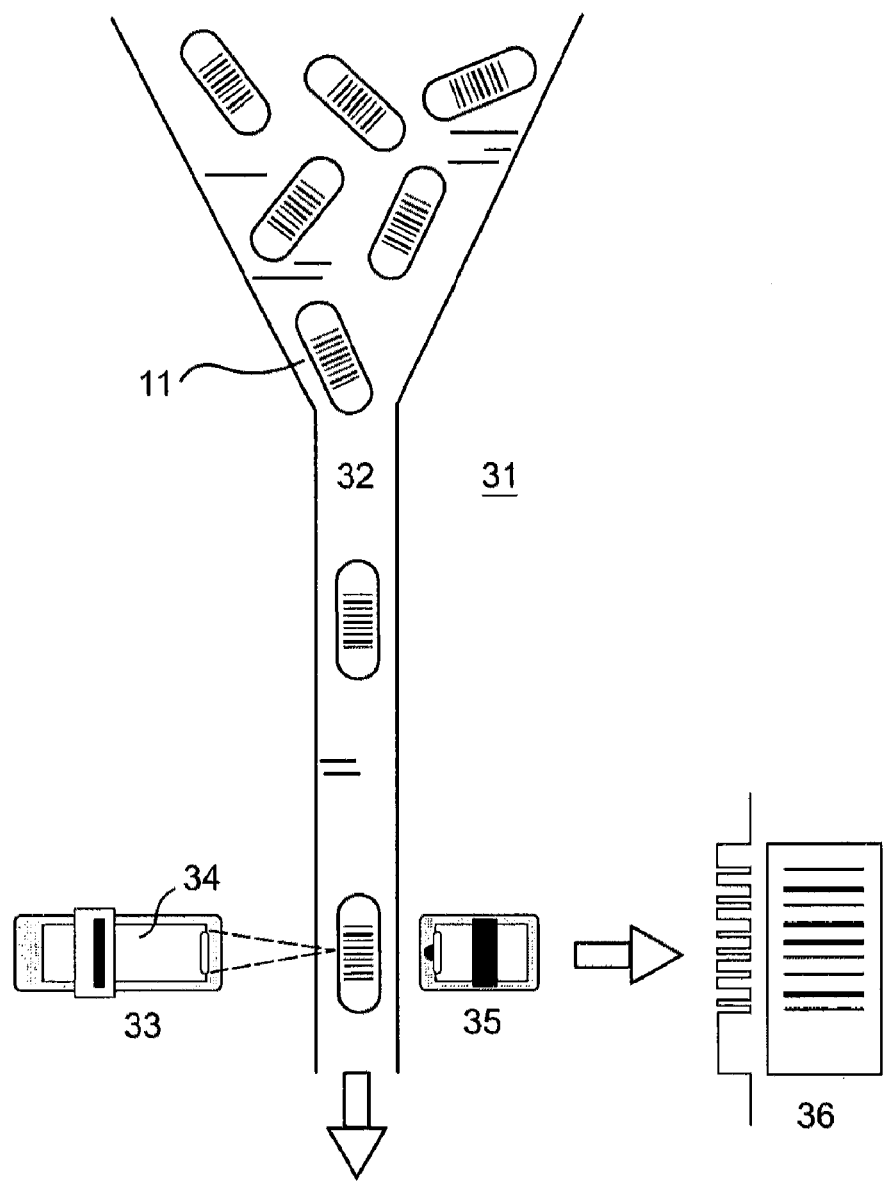
FIG. 4(a) illustrates a microfluidic apparatus in accordance with one embodiment of the present invention.

FIG. 4(a) illustrates an embodiment of a microfluidic apparatus 31 that is designed to decode the code of the LITAB 11. The microfluidic apparatus includes a micro flow channel 32 having a rectangular internal cross section sized and shaped to accommodate a single LITAB 11 in a specific desired orientation (in this case the longitudinal axis of the LITAB 11 is along the axis of the flow channel and the planar surface of the LITAB 11 is generally concentric to the wall of the channel) to flow pass a particular point in the channel. For example, the flow channel may be formed in a substrate by etching (see FIG. 8, for example). A solution carrying the LITABs flows through the micro flow channel 32, thereby causing the LITABs to flow through the micro channel 32 (e.g., in the laminar flow stream of the solution). The inlet of the micro flow channel 22 is tapered to guide the LITABs to align their longitudinal axis with the channel axis. In other words, the tapered channel inlet geometry is sized and configured to have an internal cross section with a dimension smaller than the dimension of the longitudinal axis of the LITAB 11. In another embodiment, the cross section of the micro flow channel may be axisymmetrical (e.g., a circle having a diameter large enough to accommodate the width of the LITAB 11).

The LITAB pass through a decoding zone one at a time. A decoding system, positioned with respect to the decoding zone, includes a light source and an optical sensor. In the illustrated embodiment of FIG. 4(a), the light source may be a diode laser 33 at 650 nm wavelength, with a 50× objective lens 34, and the optical sensor may be a high-speed photon detector 35 and digital readout electronics 36. Alternatively, an area light source (e.g., a laser beam having a large enough spot size) may be used to project light to simultaneously cover the entire area of the coded pattern (all the slits) on the LITAB 11, and an area optical sensor such as a CCD sensor may be used to image simultaneously the entire coded pattern and the light transmitted therethrough. Alternatively, a line scan camera may be used for the optical sensor.

As the LITABs pass through the decoding zone, light from the laser 33 is transmitted through and the light intensity is detected, by the photon detector and directly converted into 1's and 0's using threshold detection (no analog to digital conversion needed), thereby simplifying the electronics requirements. The position of the slits on the LITAB determines which of the bits is the least significant bit (LSB) and most significant bit (MSB). The slight orientation variation of the LITAB in the confined microchannel would not significantly affect the efficiency of the optical detection and consequent decoding.

More than one decoding zone having a separate decoding system may be provided along the micro flow channel 32, which may be used for detection redundancy. Further, the decoding system may include more than one set of light source and optical sensor. For example, two sets of light sources and optical sensors may be configured with orthogonal light paths through the micro flow channel 32. This decoding system would be useful if the cross section of the micro flow channel is axisymmetrical (e.g., circular cross section), such that the LITAB 11 may substantially rotate about the flow axis. Orthogonal axis decoding optics would improve orientation of the slits in relation to at least one of the decoding axis.

The flow rate through the micro flow channel may be made adjustable by using and controlling an external vacuum exhaust line pulling the flow or an external pressure supply pushing the flow. For example, an optimal flow velocity (e.g. 0.1-10 µl/s) is adjusted to secure LITAB integrity during the transportation process.

The digital readout electronic 36 (MHz-GHz) may control a line scan camera using a microcontroller or digital signal processor, which collects data from the optical sensor 35 when triggered and gated. The digital processor reads the stream of 1's and 0's that represent light intensities at intervals of 100 µs, for example, and perform rapid pattern recognition to determine the slit width sequence, based on the spacing between 1's and 0's. The LITABs 11 are configured to move at a speed of about 10-30 mm/sec, so that readout only requires about 7 milliseconds per LITAB. The readout throughput for 100,000 LITABs with 10 ms/per LITAB would require about 16 minutes per assay. Data-processing steps may be implemented by algorithms using digital signal processing software, including a c-code that quickly and efficiently processes each pattern. Details of such software are not discussed herein, since it can be developed by one skill in the art, given the functions and processes discussed herein.

An electromagnet (not shown) may be provided at the decoding zone, adjacent the micro flow channel 32, to temporarily immobilize the LITAB 11 for decoding, especially if a line scan camera is used to decode the LITAB 11. The LITAB 11, which comprises a paramagnetic material, is immobilized in the flow stream by turning on the electromagnet, and is allowed to flow down the channel by turning off the electromagnet.

The microfluidic apparatus 31 has at least two advantages: (1) it makes precise centering of the LITAB possible, thus establishing the basis for hydrodynamic illumination; and (2) it reduce the possibility of LITAB stacking across the flow stream. If we assume 1,000 LITAB in a 200 µl solution, the average spacing between beads is approximately 10 mm in the micro flow channel. It is important to have proper LITAB concentration, to ensure that the LITABs can smoothly flow into the micro flow channel 32 for optical detection. It is comparable to that of a standard cylindrical flow cell, such as flow cytometric techniques currently in use for such applications as fluorescence cell imaging.

Figure 4B:
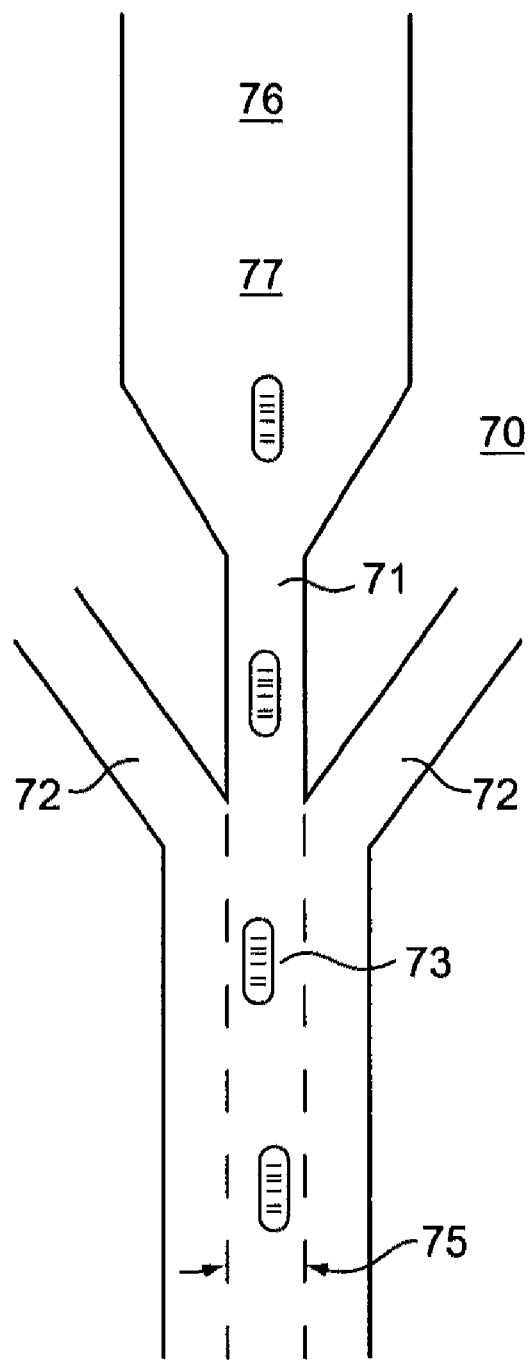
FIG. 4(b) illustrates a microfluidic apparatus that comprises a sheath flow system.

FIG. 4(*b*) illustrates another embodiment of a microfluidic apparatus that comprises a sheath flow system 70 to provide steady and stable bead flow through the optical detection area. The sheath system includes one core flow 71, which carries the barcode beads 73, and sheath flows 72, on the side of or about or around the outer periphery of the core flow 71, pulls the core flow 71 into a desired dimension. The beads are mixed in the solution in a container 76, which has a funnel 77 to deliver the beads into the core flow. To avoid the bead clogging, slightly bead agitation may be provided. Since the bead container can be fairly large in relative to the core flow, a micro tube can be used as an interface between the macroscopic container and microscopic core flow. The sheath flow, which carries liquid, such as water is at much higher speed, can be pushed or pulled by vacuum, gravity, or pressure. By adjusting the relative flow rate of core flow and sheath flow, the width 75 of the core flow can be optimized for the bead dimension. By this method, the beads will align themselves in-line and flow reliably, without wobbling or flipping, in the core flow channel through the detection zone.

Figure 8:
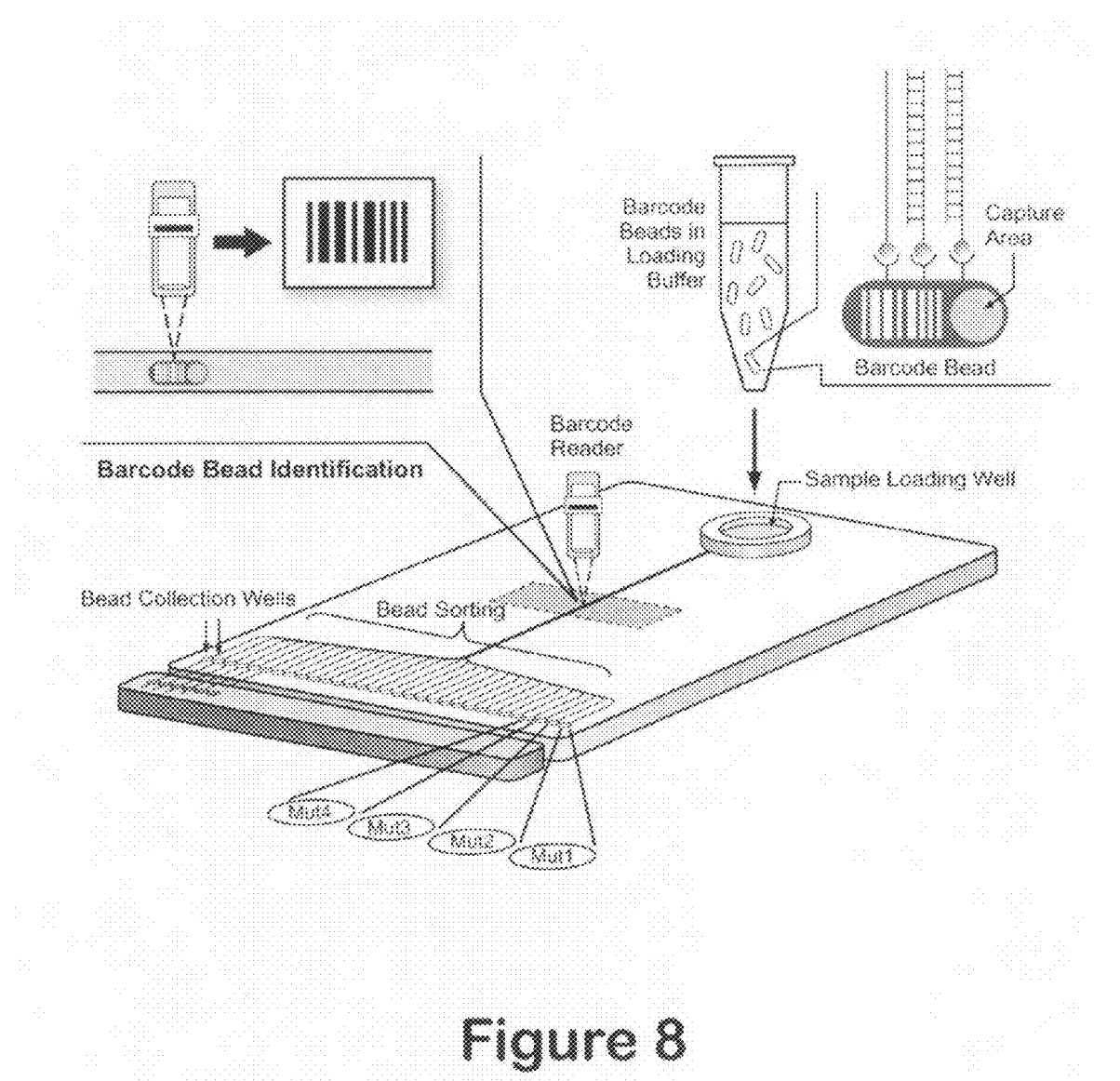
FIG. 8 illustrates a microfluidic apparatus in accordance with another embodiment of the present invention.

FIG. 8 illustrates another embodiment of a microfluidic apparatus, which provides another perspective of the overall inventive system and process.

Micro Bead Fluorescence Detection

In a further aspect of the present invention, a bioanalysis system is configured and structured for conducting bioanalysis using the coded bead of the present invention. The microfluidic system comprises the microfluidic apparatus to facilitate high throughput homogeneous or heterogeneous analysis. The detection zone of the microfluidic apparatus further includes a reaction detector (e.g., a fluorescence detector, an absorption detector, a chemiluminescent detector, etc.) for detecting the result of reactions taken place on the coded beads. In one embodiment, the assay of the microfluidic system is configured and adapted for high-throughput analysis for immunoassay, gene expression, Single Nucleotide Polymorphism (SNP) diagnostics, DNA-based tissue typing, or transcriptional profiling.

Figure 5:
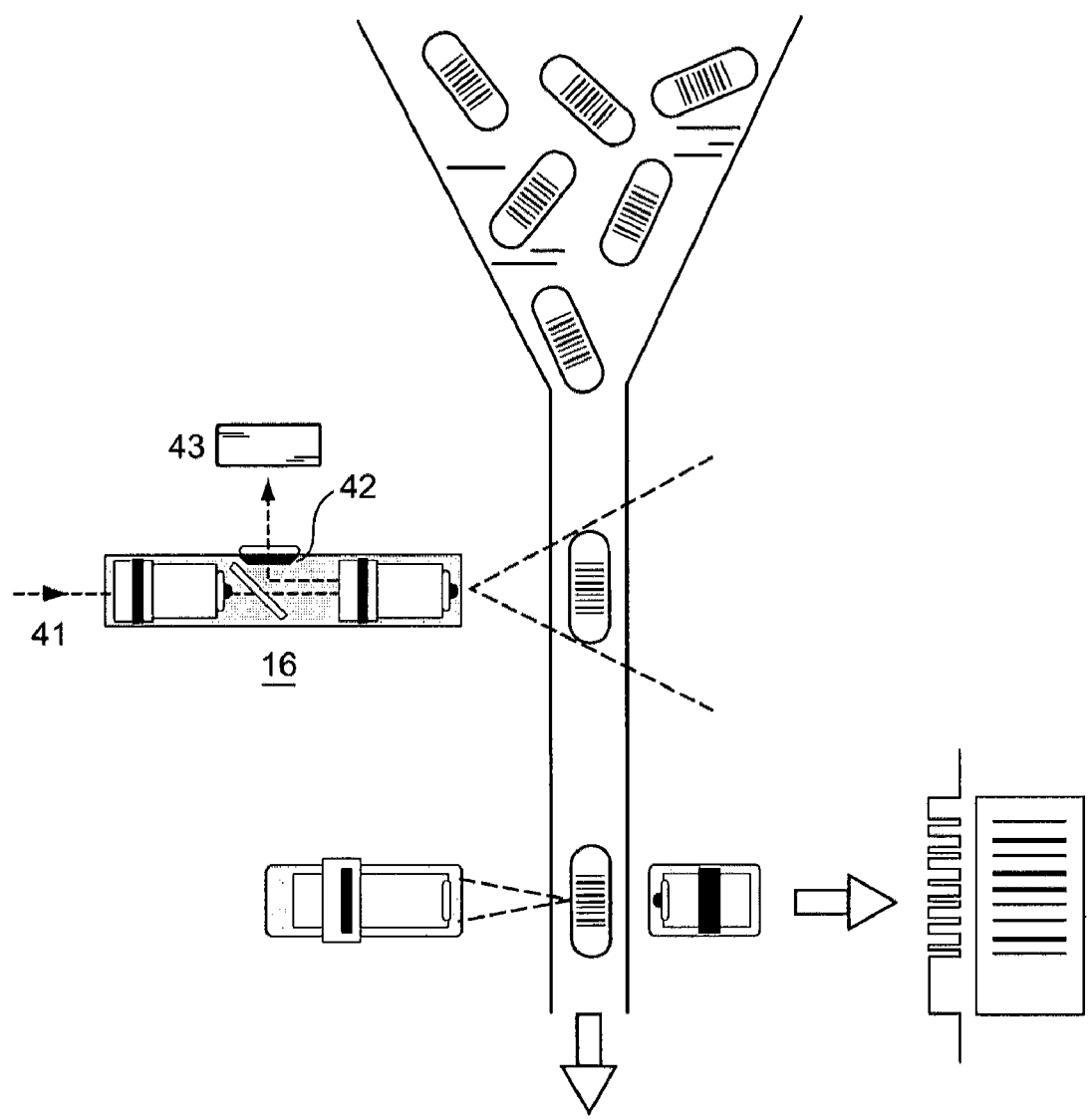
FIG. 5 illustrates a bioanalysis system comprising a microfluidic apparatus in accordance with one embodiment of the present invention.
Figure 6A:
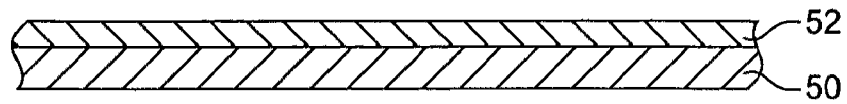
FIG. 6 illustrates the steps of forming a bead in accordance with one embodiment of the present invention.
Figure 6B:
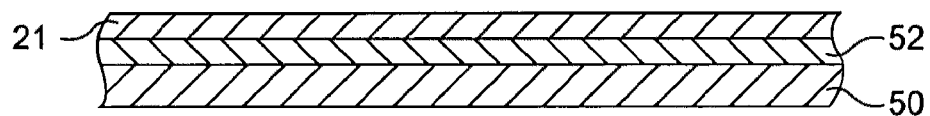
Figure 6C:
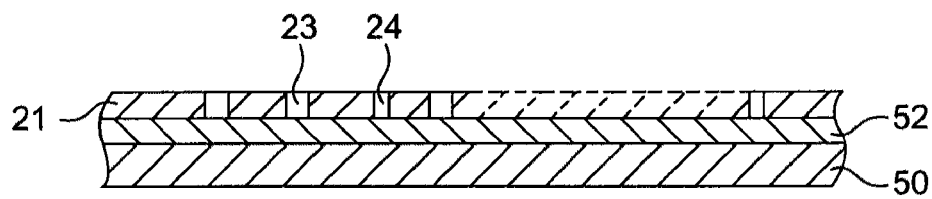
Figure 6D:
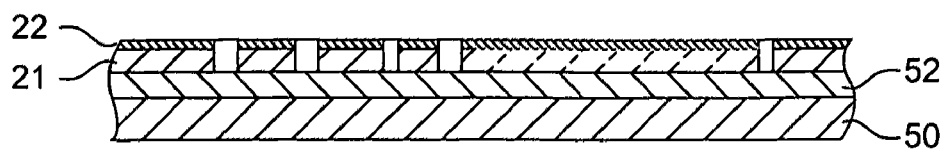

Referring to FIG. 5, one embodiment of the microfluidic system comprises essentially the microfluidic apparatus 31 shown in FIG. 4, and a detector zone upstream of the decoding zone of the micro flow channel 32. A reaction detection system 16 is positioned at the detection zone.

When the identifiable LITAB is immobilized with the capture probe, an optical label can be used for detection of positive or negative reaction. The label can be fluorescence label, chemiluminescence label, or absorption label. In one embodiment, the reaction detection system 16 may include a fluorescence detector that measures fluorescence signal from the label material on the bead. FIG. 5 shows a mixture of LITABs 11 that is introduced into the micro flow channel for fluorescence detection. When a positive fluorescence signal is detected, it indicates a positive reaction. The reaction detection system 16 comprises a light source 41, optical filter 42 and detector 43. The choice of light source depends on the fluorophore. For example, red diode laser (665 nm), and compact Argon Laser (488 nm) or Helium laser, can be the light source for Picogreen and Cy 5.5 fluorophore. Optical filter 42 removes the reflected excitation light that is mixed in the fluorescence (e.g., Picogreen: 525 nm filter and Cy5.5: 694 nm filter). Cy 3 and Cy5 are most commonly used fluorescence dyes; they can be excited with green light (530 nm) and red light (635 nm), respectively. The fluorescence intensity is commonly measured with a photomultiplier tube as the detector 43.

An electromagnet (not shown) may be provided at the reaction detection zone, adjacent the micro flow channel 32, to temporarily immobilize the LITAB 11 for reaction detection. The LITAB 11, which comprises a paramagnetic material, is immobilized in the flow stream by turning on the electromagnet, and is allowed to flow down the channel by turning off the electromagnet.

After reaction detection, the LITAB is identified downstream by decoding the code represented on the LITAB. A controller (not shown) may be provided to control and coordinate the operation of the decoding system in relation to the reaction detection system as explained below. The decoding system is triggered when a positive fluorescence signal (positive reaction) is detected by the fluorescence detector on a particular LITAB. The flow rate may be controlled (e.g., by feedback from the two zones) and/or the distance between the reaction detection zone and the decoding zone may be chosen such that a LITAB passes through the reaction detection zone substantially in parallel with another LITAB passing through the decoding zone. Further, the flow rate and/or the distance between the two zones may be chosen and controlled so that there is no intermediate LITAB present between the two zones when a LITAB is present at the reaction detection zone and another is present in the decoding zone.

Some aspects of the invention relate to the LITAB technology and its high-throughput screening application in immunoassay, antigen, antibody, pathogens, gene expression, nucleic acid hybridization, cancer diagnostics, single nucleotide polymorphisms (SNPs), and etc. Bioassays based on LITAB can be used extensively throughout the life sciences industry, drug discovery, clinical laboratory tests, and pharmacogenomics. For example, the multiplexed bioassays can be used to measure the affinity between a chemical compound and a disease target for drug discovery and development, assist physicians in prescribing the appropriate drug therapy to match the patient's unique genetic makeup, and detect genetic variations.

Some aspects of the invention relate to the LITAB is for cost-efficient automated human leukocyte antigen (HLA) typing (the HLA-TYPER system). The HLA-TYPER is designed to capture the amplified alleles onto digitally barcoded beads by hybridization, and (iii) to detect the amplified alleles (i.e. identification of the micro-pallets' bar-codes and the quantitation of the fluorescent signal emitted by the excited beads. The combination of the highly multiplexed amplification technology with the bead-based and automated microfluidic detection of the HLA-alleles offers the two following advantages over current methods for high-resolution HLA typing: the system is (i) accurate and (ii) cost-effective through reduction in labor, reagent and consumable costs. Currently there are ~3000 primer pairs for initial low resolution and ~1500 primer pairs necessary to perform subsequent high-resolution HLA typing. The platform is amenable to scale and could allow patient DNA to be screened for hundreds of different ambiguous alleles with high sensitivity and specificity at once without the necessity of tedious rounds of allele screening to increase resolution.

Some aspects of the invention relate to the LITAB is for the identification and enrichment of segments of circulating DNA in human blood that harbor mutations associated with cancer. The LITAB enriches for specific DNA segments by hybridization to complementary capture sequences on bar coded beads that are subsequently flow-sorted into different microwells. The identification of specific mutant alleles in these sorted fragments is accomplished via PCR-based screens conducted with the enriched DNA in each microwell. The method minimizes user errors and reduces labor, reagent and consumable costs. The platform is amenable to scale up and could allow thousands of different DNA segments to be screened for specific mutations with high sensitivity and specificity. The advantage of the LITAB system over existing technology is its sorting potential that enables for individual selection and enrichment of thousands of small fragments of mutant DNA from a highly complex genomic DNA suspension in a parallel fashion. This technology will enable circulating DNA in body fluids to become a powerful indicator in clinical cancer diagnostics.

Some aspects of the invention relate to the LITAB to identify genes whose SNP genotypes or haplotypes correlate with different individual drug responses, other metabolic processes or disease susceptibility. Thus the ability to quickly and accurately determine genotypes for medically relevant regions will be both critical to understanding the effects of an individual's genetic profile on these processes, and for the development of predictive, preventative and personalized medicine. The LITAB technology for use in pharmacogenetic SNP genotyping assays for medically relevant genes will allow high-throughput molecular diagnostic profiling of individuals.

The specific hybridization of DNA probes to capture probe sequences immobilized on LITABs was evaluated using oligo sequences from the published cDNA sequence of the breast cancer 1 gene, BRCA1 (NCBI Accession number NM_007294). Two 30 bp target sequences corresponding to nucleotides 317-346 from the BRCA1 cDNA sequence were used in this experiment.

Target 1 (WILDTYPE) contains the wildtype (normal) sequence. Target 2 (SNP) contains a mutant sequence with the single nucleotide polymorphism (SNP) T→C substituted at position 331. This mutation results in the amino acid substitution of an arginine residue in place of the normal cysteine residue in codon 64 of the BRCA1 protein. Each 30 bp capture probe was attached to a differently coded bead. The two bead types were co-hybridized overnight at 50° C. in solution (2×SSC, 0.1% SDS, poly dA) with a Cy5 5' labeled probe containing the complementary sequence to the Target 2 (SNP) mutant sequence. Following post-hybridization washes to remove the unbound probe the beads were immobilized on a glass slide and confocal fluorescence images were recorded. Significantly higher signals (~10×) were observed for the SNP bead over the WILDTYPE bead indicating that the SNP probe hybridization was specific to its complementary capture probe. Control staining of both bead types with propidium iodide confirmed that that the distribution of the capture probes was similar on both beads. This confirmed that the difference in Cy5 signal was due to specific hybridization of the labeled probe to the correct target. Similar results were obtained using the reverse system, where the labeled probe consisted of a DNA sequence complementary to the WILDTYPE capture probe sequence.

In comparison to the optical reflection or emissive based micro beads in the prior art, the transmission-based micro beads of the present invention not only offer improved contrast in image signal (the transmitted light would be higher in intensity than reflected light that depends on the properties of the surface reflected there from), but also present simpler optical configuration for high efficiency signal collection. High optical efficiency is important when the micro bead is in micrometer scale (e.g., the longer axis of the bead is 1 mm or less) and is analyzed in a micro flow system. The coded bead of the present invention may be manufactured by well developed and reliable semiconductor processing techniques. This manufacturing approach is also superior to existing methods. Since the bead size and coding pattern can be precisely controlled by a photomask, structures can thus be easily produced reliably in batches. In addition, since this approach is straightforward, it does not require additional complex chemistry for implementing coding elements otherwise required in existing microbeads. It is contemplated that the number of codes that can be created with the present approach can be large, by varying the number, combination and/or configuration of the transmissive and opaque sections on the bead.

LITAB Magnetic Beads in Microplate

LITABs are paramagnetic, that is, they have magnetic property when placed within a magnetic field, but retain no residual magnetism when removed from the magnetic field. This allows magnetic collection of microbeads and resuspension of the beads when the magnetic field is removed. Collection and resuspension of the digital magnetic beads can be repeated easily and rapidly any number of times. Because of the easy operation, magnetic beads are used widely in high throughput automated operation. The common robotic automation is simply putting a 96-well, 384-well or 1536-well microplate on a magnetic stand facilitated with magnetic pins by an automatic gripper. This enables washing of unbound molecules from the beads, changing buffer solution, or removing any contaminant in the solution. For example, in the case of DNA or RNA assay, the unbound or non-specific nucleotides can be removed after hybridization. While in the case of protein assay, the unbound or non-specific antibodies or antigens can be removed after the antibody-antigen reaction. Extensive washing often required during molecular biology applications to be conducted swiftly, efficiently, and with minimal difficulty. The benefit of using magnetic beads in a microplate is that it replaces expensive centrifuge for filtration and purification operations.

Barcode Decoding by Image Processing Method

In addition to decode the aligned microbeads in the microfluidic system, the randomly oriented microbeads can be decoded on a slide or in the bottom of a microplate by imaging processing method. When beads are settled down and distributed on the bottom of a planar surface in a microplate, multiple beads can be decoded simultaneously with a wide viewing or scanning image camera. Microplate is a standard format for high throughput clinical assays. Each well is used for one sample; each plate holds 96, 384, or 1,536 patient samples for 96-well, 384-well, and 1,536-well, respectively. Both bar-code image and fluorescence image can be constructed on a conventional microscope or an inverted fluorescence microscope. Therefore, an experiment can be performed in the microplate without taking the beads out. Although decoding randomly oriented beads by image processing takes slightly longer time than aligned beads in microfluidic channel, the image of the microbeads can be taken in the steady state with a better accuracy and sensitivity for decoding. The accuracy of decoding is very important for clinical diagnostics, because any false identification can lead to mis-diagnosis and mis-therapy.

The digital magnetic LITAB analytical system has a light source for bead pattern illumination and an optical CCD for capturing microbead images in the bottom of the microwell. A scanning mechanism scan all of the microwells. The CCD can be used for both barcode image and fluorescence detection. A 4M pixels CCD should have sufficient pixels to resolve the barcode pattern on beads. Optical filters are used to select the excitation wavelength and fluorescence wavelength. The preferred embodiment is using two light sources, one for barcode illumination in transmission mode and one for fluorescence excitation in reflection mode. Barcode illumination light source can be a white light, while fluorescence excitation light source need a wavelength matches with the absorption of the fluorophore. By measuring the fluorescence intensity, we can identify which beads have positive biochemical reaction. By decoding the digital barcode image, we can identify which biological probe is immobilized on the surface of that microbead.

The image is analyzed using a script written in Matlab 8.0 to decode the barcodes based on imaging pattern from the beads. The image decoding program consists of four main processes (1) Enhancement of image (2) Segmentation of beads (3) Extraction of barcode slits, and (4) Decoding of barcodes. These processes are explained in the following sections.

(1) Enhancement of image: The performance of the decoding of beads depends heavily upon the quality of the image. The accuracy of the decoding process can be improved by imaging enhancement. This image enhancement using image intensity normalization to provide uniform intensity background. Non-uniform background is often due to the non-homogeneous illumination. To achieve high image contrast of the beads, the homogeneous background should be produced first by background subtraction and normalization.

(2) Segmentation of beads: The goal of image segmentation is to outline the beads in the image for further analysis. Basic segmentation routines track boundaries such as lines, curves in images that can locate the beads in the image. We used watershed algorithm in Matlab to isolate the beads. Because the higher density of black pixels (due to opaque area) correspond to edges of the beads, the watershed transform finds ridgelines in an image and treat the surfaces enclosed by dense pixels as beads. Normally the beads have constant area and therefore each bead is separated from the image after filtering using their areas. In addition, the beads are recognized based on the slits (bars) present in the beads. The outline of the slits set is extracted using structure element transformation and filtration. With the good clarity of the slits, any noise in the background of the image is removed. The watershed algorithm in Matlab works for black and white images and so the image is converted to black and white image.

(3). Extraction of barcode slits: After segmentation of the beads, each bead is processed separately in order to extract the barcodes. The areas of beads, extracted from the main image, are considered as subimages and are processed one by one. The subimages show the orientation of the beads in random direction with major and minor axes. The angles made by the major axis of the beads with the x-axis of the image are calculated. Extraction of slits from the beads is performed after rotating the beads to x-axis. After the rotation of the beads, the borders of the beads are eliminated. Though these subimages are 2-D in nature, carries only transmission intensity information. The intensity values are averaged along the length (y-axis) of the bars. The intensity plot along the x-axis of the beads shows peaks with two widths (narrow and wide) corresponding to 1 and 0 bits.

(4). Decoding of bits: In order to decode the barcode, the widths of the transmission intensity peaks are analyzed. A half maximum line is used to calculate the widths of the peaks. In order to extract the binary bit information, five pixels are sufficient to describe the narrow slit ('0') of the beads. The widths are translated to binary bits using a tolerance of 10%. Depending on the rising or falling edges of the intensity peaks, we can identify as most significant bit (MSB) or least significant bit (LSB) of the barcodes.

Therefore, the image software consists of the following step-by-step procedure for image decoding.

Figure 9:
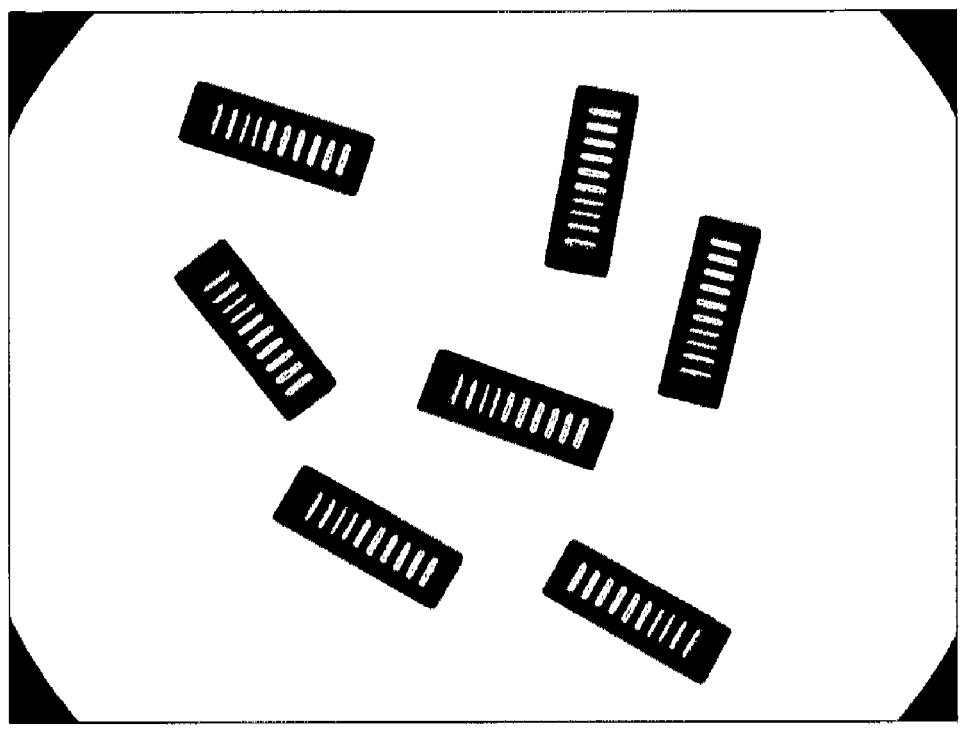
FIG. 9 illustrates the microscopic image of the barcode microbeads.

1. The images are read and converted into gray scale image as shown in the FIG. 9. Some of the images processing algorithms used in this programming are from Matlab and since they require grayscale images the images converted to gray scale images.

2. The non-uniform optical illumination of the background is eliminated. To get uniform background each image is processed using structuring element and image arithmetic. The image is subtracted from its background and the intensity of the image is adjusted in order to do further processing.

Figure 10:
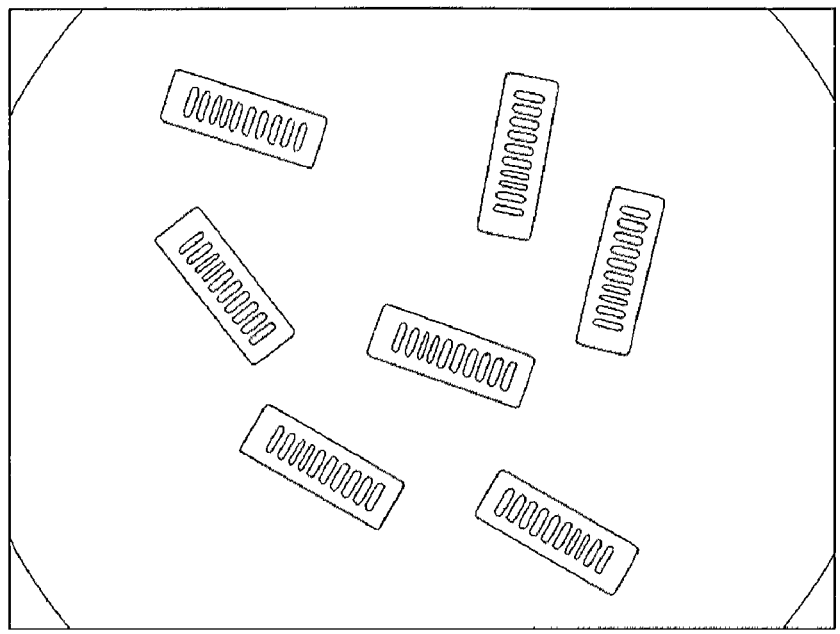
FIG. 10 illustrates the use of edge detection technique to outline the objects in the image.

3. To separate the beads edge detection is needed. The edges are detected using an edge detection technique called "sobel". The edges detected are shown in FIG. 10.

4. To separate the touching beads filtering techniques and watershed algorithm are used. Top hat with 'sobel' filtering technique is used to suppress all the edge boundaries of the bead and to highlight the slits within each bead.

5. The slits are dilated and the distance transform is used to find the watershed lines. The watershed line creation requires the images in black and white. So each image is converted into black and white using a threshold.

Figure 11:
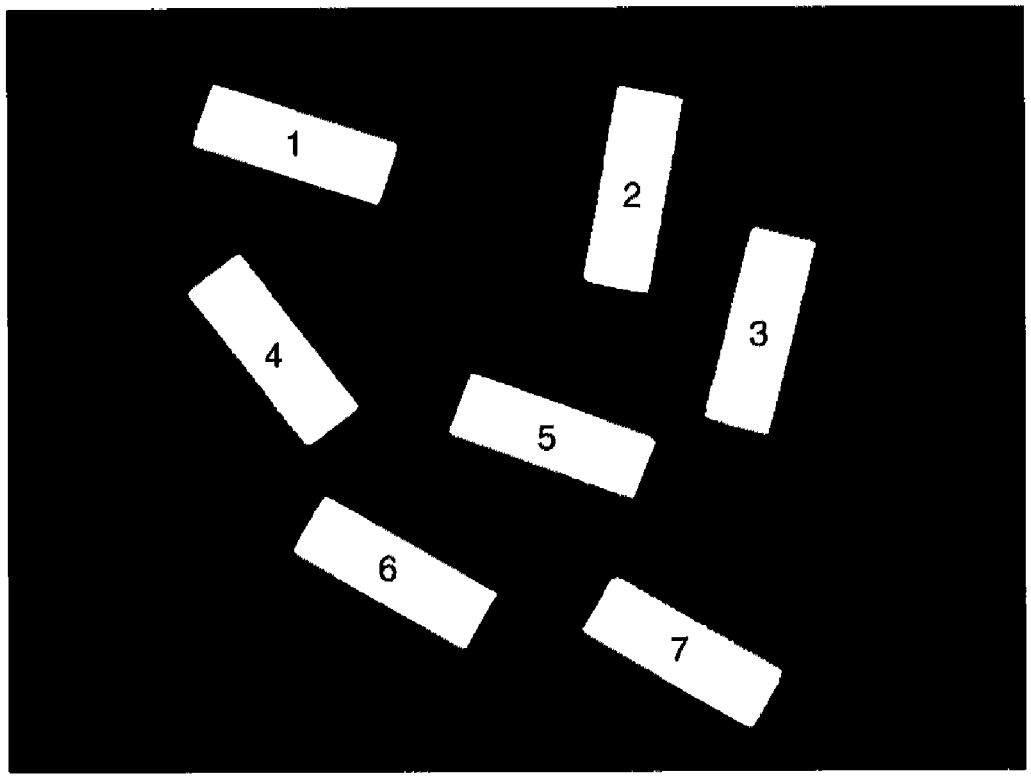
FIG. 11 illustrates segregated beads are separated using Watershed lines.
Figure 12:
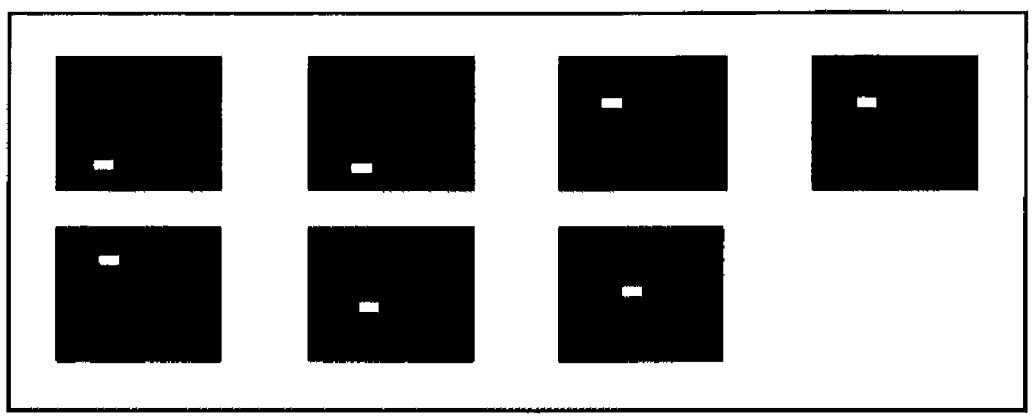
FIG. 12 illustrates the method of aligning each microbead to the major axis, and the gray scale image is converted into a matrix, which contained the pixel values.
Figure 13:
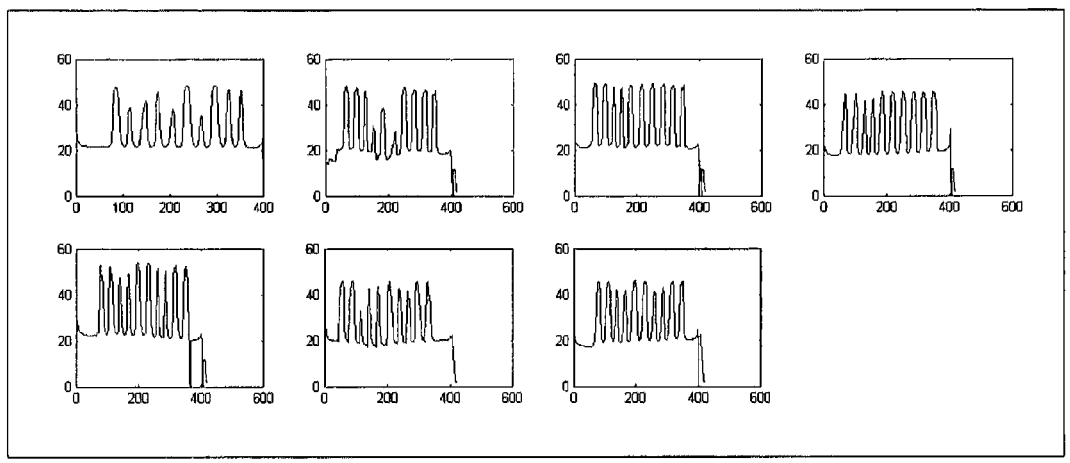
FIG. 13 shows that the bead image is converted to gray scale intensity as a function of pixel values.

6. Rectangular structural elements of the barcode slits are assumed and image dilation is carried out. Using the distance transform of the image, watershed lines are created. The watershed algorithm also requires the magnitude of the gradient of the filtered images for processing the watershed lines.
7. Once the watershed lines are created the edge detected image are superimposed with the watershed lines to get the resultant separated beads. These separated beads though irregular at the edges, the 1-D barcodes are intact.
8. Once the beads are separated as individual regions in the image, the regions are labeled (FIG. 11) using a RGB color code or by numbering each bead. Different parameters such as area, angle of orientation, pixel list are calculated for each bead using the region pops algorithm.
9. To align each microbead to the major axis (FIG. 12), the original gray scale image is taken and converted into a matrix, which contained the pixel values. Pixel index list of the microbeads are obtained from the region properties. The gray scale image is replaced with the pixel index list of each microbead and the rest of the pixels are made zero. Using the angle of orientation of each microbead calculated earlier, each bead is rotated along the major axis.
10. The microbead images are displayed by plotting the intensity versus pixel number as shown in FIG. 13. Each intensity plot is analyzed to get the barcode in the microbead. A line is drawn parallel to the x-axis and the x values are taken for each intersection of the line with the plot. Then the differences between two consecutive x values are obtained. The alternative values are the widths of the barcodes in each microbead. The direction of the barcode is found by calculating the spacing between the edges of the barcode and the first slit. Longer distance corresponds to the forward direction of reading the barcodes. If a bead appears reversely in the image the barcode bits are reversed. The decoded results are displayed as shown in FIG. 14.

While the invention has been described with respect to the described embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

The invention claimed is:

1. A digital magnetic microbead analytical system comprising
   a. a microplate with a plurality of wells for receiving microbeads;
   b. digital magnetic microbeads to be loaded at the bottom of the wells of said microplate;
   c. two light sources, with different wavelengths, one for barcode image illumination and one for fluorescence illumination,
   d. an optical detector, located above or under said microplate, to be used to image said digital magnetic microbeads; and
   e. an image software to be used to decode the image pattern and detect the fluorescence of said magnetic microbeads wherein
   f. said image illumination is in transmission mode, while said fluorescence illumination is in reflection mode, and said optical detector can separately or sequentially detect the transmission signal and fluorescence signal the said microbead; and
   g. said two light sources are configured with orthogonal light paths through the largest planar surface of the microbeads
   wherein the microbeads comprise a body; a first photopolymer layer; a second photopolymer layer; and an intermediate layer between the first layer and the second layer, the intermediate layer having an encoded pattern defined thereon, wherein the intermediate layer is partially substantially transmissive and partially substantially opaque to light, representing a code corresponding to the micro bead wherein the outermost surface of the microbead comprises said photoresist photopolymer and said photoresist photopolymer is functionalized with a specific target or capture molecule selected from the group consisting of proteins, nucleic acids and small molecules and wherein said micro bead has about the same density as water.

2. The microbead analytical system of claim 1, wherein (a) said microbeads are randomly distributed on the surface of said microplate, (b) said each microbead has most significant bit (MSB) and least significant bit (LSB) for barcode orientation identification.

3. The microbead analytical system of claim 2, wherein said microbeads is illuminated with a light source, the contrast of "1" and "0" barcode, based on the ratio of either the total intensity of the transmission peak or bandwidth of the transmission peak, is more than 1.5.

4. The microbead analytical system of claim 1, wherein the intermediate layer comprises a series of alternating substantially light transmissive sections and substantially light opaque sections defining the encoded pattern.

5. The microbead analytical system of claim 1, wherein relative positions, widths and/or spacing between the transmissive sections and/or opaque sections represent a binary code.

6. The microbead analytical system of claim 1, wherein the substantially light opaque sections comprises a light blocking material.

7. The microbead analytical system of claim 1, wherein the body of each microbead has a longest orthogonal axis of 1 mm or less.

8. The microbead analytical system of claim 1, wherein the first layer and the second layer are functionalized with a material selected from the group consisting of proteins, nucleic acids, small molecules, chemicals, and combinations thereof.

9. The microbead analytical system of claim 1, wherein the light transmissive sections are defined by slits through the intermediate layer, and the light opaque sections are defined by a light reflective material and/or a light absorptive material.

10. The microbead analytical system of claim 9, wherein the slits comprise slits of a first width and slits of a second width, and wherein the first width represents a "0" and the second width represents a "1" in a binary code.

11. The microbead analytical system of claim 10, wherein the first width is about 1 to 10 microns and the second width is about 1 to 50 microns, and wherein the first width is narrower than the second width.

12. The microbead analytical system of claim 10, wherein said binary codes can be decoded by image software.

* * * * *